(12) United States Patent
Zahavy

(10) Patent No.: US 11,306,344 B2
(45) Date of Patent: Apr. 19, 2022

(54) SPECTRAL INTENSITY RATIO (SIR) ANALYSIS FOR RAPID LIVE MICROBIAL ENUMERATION

(71) Applicant: TACOUNT EXACT LTD., Netanya (IL)

(72) Inventor: Eran Zahavy, Lod (IL)

(73) Assignee: TACOUNT EXACT LTD., Netanya (IL)

( * ) Notice: Subject to any disclaimer, the term of this patent is extended or adjusted under 35 U.S.C. 154(b) by 516 days.

(21) Appl. No.: 15/542,922

(22) PCT Filed: Jan. 9, 2016

(86) PCT No.: PCT/IB2016/050094
§ 371 (c)(1),
(2) Date: Jul. 11, 2017

(87) PCT Pub. No.: WO2016/113655
PCT Pub. Date: Jul. 21, 2016

(65) Prior Publication Data
US 2018/0010165 A1 Jan. 11, 2018

Related U.S. Application Data

(60) Provisional application No. 62/102,506, filed on Jan. 12, 2015.

(51) Int. Cl.
*C12Q 1/06* (2006.01)
*C12Q 1/04* (2006.01)
*G01N 1/30* (2006.01)

(52) U.S. Cl.
CPC ............ *C12Q 1/06* (2013.01); *C12Q 1/04* (2013.01); *G01N 1/30* (2013.01)

(58) Field of Classification Search
CPC ............ C12Q 1/06; C12Q 1/04; G01N 1/30
See application file for complete search history.

(56) References Cited

U.S. PATENT DOCUMENTS

| 5,534,416 A | 7/1996 | Millard et al. |
| 5,545,535 A | 8/1996 | Roth et al. |
| 8,241,866 B2 * | 8/2012 | Yoshida ................... C12Q 1/34 435/29 |
| 9,290,790 B2 | 3/2016 | Azevedo Pina Vaz et al. |
| 2011/0177549 A1 * | 7/2011 | Glukhman ............... C12Q 1/06 435/39 |
| 2013/0324437 A1 | 12/2013 | Pogliano et al. |

FOREIGN PATENT DOCUMENTS

| CN | 102089419 A | 6/2011 |
| CN | 101287843 B | 11/2012 |
| JP | H02-281131 A | 11/1990 |
| JP | H07-196930 A | 8/1995 |
| JP | 2002-168870 A | 6/2002 |
| JP | 2002-291499 A | 10/2002 |
| JP | 2007-060945 A | 3/2007 |
| JP | 2011-527562 A | 11/2011 |
| JP | 2013-538567 A | 10/2013 |
| WO | WO-2011/086990 A1 | 7/2011 |

OTHER PUBLICATIONS

Nishikawa, Sumio, "Fluorescent AM 1-43 And FM1-43 Probes For Dental Sensory Nerves And Cells: Their Labeling Mechanisms And Applications", Japanese Dental Science Review, vol. 47, Issue 2, Aug. 2011, pp. 150-156. (Year: 2011).*
Nuding et al., A Flow Cytometric Assay To Monitor Antimicrobial Activity Of Defensins And Cationic Tissue Extracts, 2006, Journal Of Microbiological Methods, vol. 65, pp. 335-345. (Year: 2006).*
International Search Report and Written Opinion issued in corresponding application No. PCT/IB2016/050094 dated Mar. 18, 2016.
Kerstens et al., "Flow Cytometric Enumeration of Bacteria Using TO-PRO-3 Iodide as a Single-Stain Viability Dye," Journal of Laboratory Automation, vol. 19, No. 6, 2014, pp. 555-561.
Nuding et al., "A flow cyometric assay to monitor antimicrobial activity of defensins and cationic tissue extraxts," Journal of Microbiological Methods, vol. 65, No. 2, 2006, pp. 335-345.
Wang et al., "Antimicrobial specificity and mechanism of action of disulfide-removed linear analogs of the plant-derived Cys-rich antimicrobial peptide Ib-AMP1", Peptides, vol. 30, 2009, pp. 2144-2149.
International Preliminary Report on Patentability issued in corresponding application No. PCT/IB2016/050094 dated Mar. 28, 2017.
E. Bogomolny et al., "Dead/alive bacteria detection using an all-fibre optical system", Progress in Biomedical Optics and Imaging, SPIE—International Society for Optical Engineering, Mar. 13, 2014, pp. 1-8, vol. 8933, Bellingham, WA, US.

* cited by examiner

*Primary Examiner* — Louise W Humphrey
*Assistant Examiner* — Anjali Ajit Hirani
(74) *Attorney, Agent, or Firm* — Foley & Lardner LLP

(57) ABSTRACT

Single dye fluorescent staining (with a membrane-associated dye such as FM 1-43 or FM 4-64) and the combination of differences in both intensity and spectral emission discriminate live from inactivated/dead bacteria and provides for rapid and accurate detection of live bacteria in mixed populations.

10 Claims, 14 Drawing Sheets

SPECTRAL INTENSITY RATIO (SIR) ANALYSIS FOR RAPID LIVE MICROBIAL ENUMERATION

CROSS-REFERENCE TO RELATED APPLICATIONS

This application is a national stage application under 35 U.S.C. § 371 of International Application No. PCT/IB2016/050094, filed Jan. 9, 2016, which claims the benefit of U.S. Provisional Application No. 62/102,506, filed Jan. 12, 2015 the contents of each of which is hereby expressly incorporated by reference in its entirety.

FIELD OF THE INVENTION

Described is a method for rapidly measuring the number of live bacteria in a sample. The method is useful for, e.g., quantitatively validating the efficiency of different disinfection procedures that are abundant in many industries such as pasteurizing, chlorinating, UV, Ozone and for assessing the number of live organisms in food or water for consumption.

BACKGROUND OF THE INVENTION

The level of bacteria in a sample is of great interest to e.g. food and water intended for human and animal consumption. Many industries such as water and beverages companies, food industries, pharmaceuticals, etc., use various disinfection methods for assuring that no bacteria, or minimal amount of bacteria, are left alive in the product after the disinfection procedures.

Quantification of live microorganisms is typically a specialized laboratory procedure based upon a bacteria culture growing. Specific conditions for microbial growth on solid and liquid media need to be maintained over long incubation times at the end of which is determined the number of colony forming units (CFU) per unit of volume (e.g. CFU/ml). In the laboratory, the CFU is typically calculated by normalizing the total number of counted colonies according to the number of dilutions and the volume of the sample. This methodology requires laboratory equipment, qualified personnel and long time periods which may range from one day to one month. The common procedure is spreading a sample on agar plates and incubating them for a period of hours or sometimes days and then counting the number of colonies that grow on the plates. For microorganisms that do not grow on solid medium, and sometimes for anaerobic organisms, the standard is "most estimated count" (MEC). (Holms W., J. Gen. Microbiol. 54: 255-260 (1968); Bridgewater L., American Public Health Association, American Water Works Association, and Water Environment Federation, *Standard Methods for the Examination of Water and Wastewater*. Edited by Eugene W. Rice. 22nd ed. Washington, D.C.: American Public Health Association, 2012). This method uses tube serial dilution and visualisation of the liquid transparency followed by calculation of starting microbial concentration. Methods that require culturing bacteria are, however, slow, expensive, and can be affected by bacteria clumping, the type of culture media on which the organism grows, and the presence of dead cells and debris. Additionally, some bacteria will not grow in culture.

It would therefore be advantageous for many industries to have a rapid tool for validating their disinfection protocol by discriminating between live and inactivated bacteria without relying on a culture based assay.

SUMMARY OF THE INVENTION

The method of the present invention utilizes single dye fluorescent staining and analysis to create a novel tool for rapid detection of live bacteria. In the method of the present invention, differences in both intensity and spectral emission are combined to discriminate live from inactivated bacteria.

In one embodiment, the present application provides a method for differentiating between live and inactivated bacteria in a treated sample comprising: staining the sample with a single membrane-associated dye; illuminating the sample with an incident light at $\lambda$ excitation; measuring, for each bacterial cell (i) the intensity I1 of emitted light at wavelength $\lambda 1$; and (ii) the intensity I2 of emitted light at wavelength $\lambda 2$; calculating a ratio I2/I1; and determining whether the bacterial cell is live or inactivated based on whether the calculated I2/I1 is larger or smaller than a predetermined threshold. In another embodiment, this same process may be conducted for a whole sample rather than for each cell individually, measuring whole sample intensity.

In some embodiments, fluorescence analysis, flow cytometry and microscopy may be used. Further embodiments, such as (but not limited to) those involving flow cytometry and microscopy, employ single bacteria detection and quantification.

The test sample to be analyzed may be a liquid, semi-liquid or dry sample. In one embodiment, the sample may be obtained from drinking water, a food or a beverage. In a different embodiment, the sample is obtained from a pharmaceutical product, a personal care product, or a body fluid. Body fluids may include, but are not limited to, plasma, saliva, urine, a throat sample, or gastrointestinal fluid. In yet another embodiment, the sample is obtained from a municipal water system, a well, potable water, wastewater, a natural water source, recreational water or a soil. In a different embodiment, the test sample is from a medical device. Preferably, the medical device is an implant, a patch or a valve.

In some embodiments the membrane-associated dye is a styryl dye. In a preferred embodiment, the membrane-associated dye is FM® 1-43 (43N-(3-Triethylammonium-propyl)-4-(4-(Dibutylamino) Styryl) Pyridinium Dibromide) or FM® 4-64 (N-(3-Triethylammoniumpropyl)-4-(6-(4-(Diethylamino) Phenyl) Hexatrienyl) Pyridinium Dibromide). In some embodiments, the excitation wave length is between about 360 nm and about 600 nm and the wavelengths at which I1 and I2 are measured are between about 520 and about 720 nm. In a preferred embodiment, the excitation wavelength is 488 nm and the emission wavelengths at which I1 and I2 are measured are 530 nm and 610 nm, respectively. In other embodiments, the excitation wave length is between about 360 nm and about 600 nm and the wavelengths at which I1 and I2 are measured are between about 600 and about 800 nm. In such embodiment, the excitation wavelength is in the range of 488 to 570 nm and the emission wavelengths at which I1 and I2 are measured are 670 nm and 780 nm, respectively.

The foregoing general description and the detailed description are exemplary and explanatory and are intended to provide further explanation of the invention as claimed. For detailed understanding of the invention, reference is made to the following detailed description of the preferred embodiments, taken in conjunction with the accompanying drawings. Other objects, advantages and novel features will be readily apparent to those skilled in the art from the following detailed description of the invention.

BRIEF DESCRIPTION OF THE DRAWINGS

FIG. 6A Live bacteria; FIG. 6B Heated (85° C., 15 min), FIG. 6C Chlorinated, FIG. 6D. Ethanol 70%, FIG. 6E. UV-Low Pressure, FIG. 6F UV-Medium Pressure. The flow cytometry dot plot is gated by light scatter parameters (FSC/SSC) for the bacterial population, the fluorescence filter are: 530(30) nm and 610(20) nm. Excitation was by 488 nm laser. All inactivated samples (in 6B.-F.) showed 5 to 6 log counting reduction by cfu. The number for X and Y in the dot-plots represent the mean values of the emission at 530 and 610 nm respectively within the marked gate.

FIG. 8A. Live (black dots) vs heated (85° C., 5 min) inactivation (grey dots); FIG. 8B. Live (black dots) vs chlorine inactivation (grey dots); FIG. 8C. Live (black dots) vs UV-MP inactivation (grey dots). The flow cytometry dot plot is gated by light scatter parameters (FSC/SSC) for the bacterial population. The fluorescence filter are: 670(14) nm and 780(60) nm. Excitation was by 561 nm laser.

FIGS. 12A1-A3, B1-B3 was produced using microscopy fluorescence imaging, Excitation.=470 nm, Emission=525 (50) nm, of E. coli FM® 1-43 (43N-(3-Triethylammoniumpropyl)-4-(4-(Dibutylamino) Styryl) Pyridinium Dibromide) stained. [[F]] FIGS. 12A1-A3: Live bacteria. I=35 (±5) GL. FIGS. 12B1-B3: Heated inactivated bacteria. I=40 (±10) GL. Gray level (GL) analysis performed by Fiji software per object.

FIG. 13A: Live bacteria. I=20-50 GL.

FIG. 13B: Heated inactivated bacteria. I=128(±20) GL. FIG. 13C: Chlorinated inactivated bacteria. I=135(±20) GL. The sample were treated 5 min with 10 mM thiosulfate before microscopic measurements. FIG. 13D: Ethanol 70% inactivated bacteria. I=90(±10) GL. FIG. 13E: UV-MP inactivated bacteria. I=120(±20) GL. Gray level (GL) analysis performed by Fiji software per object.

DETAILED DESCRIPTION

Figure 1:
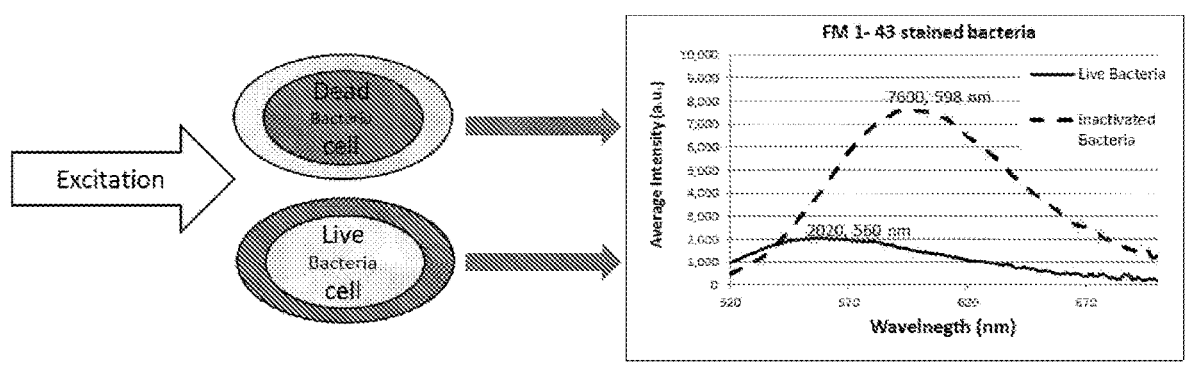
FIG. 1 is a schematic representation of the spectral detection of the stained bacteria and the spectral/intensity discrimination between live and inactivated bacteria.

The present invention is based on the finding that that upon staining bacteria with fluorescent membrane dyes such as styryl dye the emission fluorescence of live bacteria versus inactivated bacteria are weaker and shifted. Such phenomena might be the result of the interaction of the dyes in the lipophilic membrane environment in the live cells, versus the inactivated cells where the dyes are inserted to the more hydrophilic environment of the cytoplasm.

As used herein, "live cell" or "live bacteria" means a bacterial cell which has the potential to grow and divide. "Dead" and "inactivated" are used interchangeably to refer to dead bacterial cells.

The present invention relates to a method for differentiating between live and inactivated bacteria. The method is performed using spectral intensity ratio analysis of cell membrane dyes. The method is based on the discovery that, upon excitation of a specimen at a specific wavelength, measurable differences are evident in both the maximum emission peak and emission intensity between live and inactivated bacteria. Accordingly the ratio of emission intensities at two designated wavelengths or spectral intensity ratio (SIR)—I2/I1—can be used as a means of differentiating live bacteria from inactivated bacteria. The method of the present invention allows accurate and rapid differentiation of live from inactivated cells through relying on excitation/emission based analysis rather than culture based validation, as well as requiring the use of only one dye to successfully differentiate. Thus, the method includes steps of: staining the sample with a single membrane-associated dye; illuminating the sample with an incident light at $\lambda$ excitation; measuring, for each bacterial cell (i) the intensity I1 of emitted light at wavelength $\lambda 1$; and (ii) the intensity I2 of emitted light at wavelength $\lambda 2$; calculating a ratio I2/I1; and determining whether the bacterial cell is live or inactivated based on whether the calculated I2/I1 is larger or smaller than a predetermined threshold. In another embodiment, this same process may be conducted for a whole sample rather than for each cell individually. In further such embodiments, bulk intensity may be measured to determine whether the sample contains live or inactivated bacteria.

The system to perform the method of the invention is preferably a device capable of excitation of the membrane-associated dye and measuring emission intensity at the prescribed wavelengths $\lambda 1$ and $\lambda 2$, such as (but not limited) to a flow cytometer, fluorescent microscope, or other instrument capable of fluorescence analysis.

The emission spectrum profile is measured with a spectral analyser or emission filters. The excitation wavelength is between about 360 nm and about 600 nm and the wavelengths at which I1 and I2 are measured are between about 520 and about 800 nm. In a preferred embodiment, the excitation wavelength is 488 nm and the emission wavelengths at which I1 and I2 are measured are 530 nm and 610 nm, respectively. For FM® 4-64 (N-(3-Triethylammoniumpropyl)-4-(6-(4-(Diethylamino) Phenyl) Hexatrienyl) Pyridinium Dibromide) the excitation wavelength could be in between 488 to 570 nm and the emission wavelengths at which I1 and I2 are measured are 670 nm and 780 nm, respectively In a preferred embodiment, each bacterial cell is classified as live or inactivated based on the SIR value (I2/I1) relative to the prescribed threshold.

In some embodiments, the process of determining whether the bacterial cell is live or inactivated based on whether the calculated SIR of the sample is larger or smaller than a predetermined threshold involves a non-viability parameter (NVP) calculated by dividing the SIR of the sample by the SIR of a control of live bacteria. Said NVP is then compared to a threshold value to determine if the bacteria are live or inactivated. In further embodiments, an NVP of about 1 would indicate live bacteria while an NVP significantly greater than 1 would indicate dead bacteria. In some embodiments, where the SIR is calculated for the whole sample, the concentration of the control of live bacteria should be the same as the test sample.

In further embodiments, where the test sample contains a homogeneous bacterial population or heterogeneous bacterial population in a known ratio, a standard curve of SIR values for a control of live bacteria can be used to establish the predetermined threshold for determining whether the bacterial cell is live or inactivated.

Dyes include but are not limited to fluorescent dyes which incorporate into the lipid bilayer. Examples of fluorescent dyes include styryl dyes and cyanine dyes. Representative styryl dyes include FM® 1-43 (43N-(3-Triethylammoniumpropyl)-4-(4-(Dibutylamino) Styryl) Pyridinium Dibromide), FM® 1-43FX (Fixable analog of 43N-(3-Triethylammoniumpropyl)-4-(4-(Dibutylamino) Styryl) Pyridinium Dibromide), FM® 4-64 (N-(3-Triethylammoniumpropyl)-4-(6-(4-(Diethylamino) Phenyl) Hexatrienyl) Pyridinium Dibromide) and FM® 4-64FX (fixable analog of N-(3-Triethylammoniumpropyl)-4-(6-(4-(Diethylamino) Phenyl) Hexatrienyl) Pyridinium Dibromide), FM® 2-10 (N-(3-Triethylammoniumpropyl)-4-(4-(Diethylamino)styryl)Pyridinium Dibromide) dye. Representative cyanine dyes include Cy2, Cy3, Cy3B, Cy3.5, Cy5, Cy5.5 and Cy7. FM® 1-43 is N-(3-Triethylammoniumpropyl)-4-(4-(Dibutylamino)Styryl)Pyridinium Dibromide, purchased from Life Technology (#T-35356), and also sold by Sigma as "Synaptogreen" (#56814). FM® 4-64 is N-(3-Triethylammoniumpropyl)-4-(6-(4-(Diethylamino) Phenyl) Hexatrienyl) Pyridinium Dibromide purchased from Life Technology (#T-13320) or Sigma as "Synaptored" (#S6689).

More than one dye can be used, but the present method may be performed with a single dye. The use of a single dye not only simplifies the method, but reduces variability caused by the presence of two dyes.

The test sample to be analyzed may be a liquid, semi-liquid or dry sample. The sample may be obtained from drinking water, a food or a beverage, a pharmaceutical product, a personal care product, or a body fluid. Body fluids may include, but are not limited to, plasma, saliva, urine, a throat sample, or gastrointestinal fluid. Test samples may also be obtained from a municipal water system, a well, potable water, wastewater, a natural water source, recreational water or a soil. In different embodiments, test samples are obtained from medical devices. Examples of medical devices include, but are not limited to, implants, patches and heart valves.

In some embodiments, the test sample may be analyzed for success or failure of a bacterial inactivation treatment, such as (but not limited to) antibiotic or antibacterial treatment, Chlorine inactivation, heating, Ethanol, and UV irradiation by medium pressure. In further embodiments, a threshold value can be determined by taking the I2/I1 of a pre-treatment sample and then compared to the I2/I1 of the test sample to determine efficacy of the bacterial inactivation treatment.

Bacteria may include, but are not limited to, coliform bacteria, enterobacteria, *Salmonella, Listeria, Shigella, Pseudomonas, Staphylococcus* or *Methanobacterium.*

The following examples are set forth as representative of specific and preferred embodiments of the present invention. These examples are not to be construed as limiting the scope of the invention in any manner. It should be understood that many variations and modifications can be made while remaining within the spirit and scope of the invention.

Materials and Methods

Dyes: N-(3-Triethylammoniumpropyl)-4-(4-(Dibutylamino) Styryl) Pyridinium Dibromide purchased from Life Technology as FM® 1-43 (#T-35356) or Sigma as "Synaptogreen" (#S6814). N-(3-Triethylammoniumpropyl)-4-(6-(4-(Diethylamino) Phenyl) Hexatrienyl) Pyridinium Dibromide purchased from Life Technology as FM® 4-64 (#T-13320) or Sigma as "Synaptored" (#S6689).

Bacteria: Unless otherwise stated, bacteria were purchased from Biological Industries, Beit Haemek, Israel. Dried bacteria was recovered according to ATCC instruction and aliquots were stored in glycerol in −20° C.

| | |
|---|---|
| E. coli | ATCC (#8739) |
| E. coli | ATCC (#25922) |
| E. coli O157:H7 (EHEC) | |
| E. aerogenes | ATCC (#13048) |
| E. cloacae | ATCC (#23355) |
| C. freundii | ATCC (#8090) |
| K. pneumonia | ATCC (#13883) |
| E. faecalis | ATCC (#19433) |
| E. faecalis | ATCC (#35550) |
| E. faecium | ATCC (#19434) |
| S. aureus | ATCC (#25923) |
| B. subtilis | ATCC (#6633) |
| Ps. Aeruginosa | ATCC (#9027) |
| Ps. Aeruginosa | ATCC (#27853) |

Bacterial inactivation: Bacteria in phosphate buffered saline (PBS) were inactivated by one of the following procedures: Pasteurization (Heating)—85° C., 5-15 min; Chlorine (Sodium-hypochlorite)—0.01%, 10 min; Ethanol—70%, 10 min; UV-MP irradiation—4-70 mJ, medium pressure lamp (200-300 nm) in Atlantium Tech. LTD; UV-LP irradiation: 4-70 mJ, Low pressure lamp (254 nm) in Atlantium Tech. LTD.

Microscopy: Live or inactivated bacteria was stained with FM® 1-43(43N-(3-Triethylammoniumpropyl)-4-(4-(Dibutylamino) Styryl) Pyridinium Dibromide) (4.9 µM) or Synaptored (15 µM) in PBS for 5 min in room temperature. Using TACounts unique filtration system, the sample was filtered through a polycarbonate membrane with 0.4 µm cutoff. The filter was washed using 1 ml PBS and then imaged using a fluorescence microscope (Axio Scope A1, Zeiss, Germany).

Excitation/emission filters based on Cube38 in the Zeiss setup. For FM® 1-43 (43N-(3-Triethylammoniumpropyl)-4-(4-(Dibutylamino) Styryl) Pyridinium Dibromide)—Excitation: 470 (±20) nm, Beam Splitter FT495, Emission: BP 525 (±25) nm or 600 (±25) nm. For FM® 4-64 (N-(3-Triethylammoniumpropyl)-4-(6-(4-(Diethylamino) Phenyl) Hexatrienyl) Pyridinium Dibromide)—Excitation: 535±25 nm, Emission: 590LP.

Quantitative microscopic image analysis was conducted using Fiji software. Gray levels (GL) are independent of color and indicate the brightness of individual pixels, taking into account color sensitivity of the human eye.

Flow Cytometry: Live or inactivated bacteria was stained with FM® 1-43 (43N-(3-Triethylammoniumpropyl)-4-(4-(Dibutylamino) Styryl) Pyridinium Dibromide) (4.9 µM) or FM® 4-64 (N-(3-Triethylammoniumpropyl)-4-(6-(4-(Diethylamino) Phenyl) Hexatrienyl) Pyridinium Dibromide) (15 µM) in PBS for 5 min in room temperature. Preliminary work showed that immediate measurements does not require washing steps. The samples were measured using fluorescent activated cell sorting (FACS. Here, FACSARIA III, BD, USA, was used). The optical setup for FM® 1-43 (43N-(3-Triethylammoniumpropyl)-4-(4-(Dibutylamino) Styryl) Pyridinium Dibromide) stained bacteria include light scatter parameter by the primary 488 nm excitation and FSC/SSC detector and fluorescence measurements using band path filters of 530 (±15) nm, 610 (±10) nm. For the FM® 4-64 (N-(3-Triethylammoniumpropyl)-4-(6-(4-(Diethylamino) Phenyl) Hexatrienyl) Pyridinium Dibromide) stained bacteria the fluorescence parameters were detected by the 561 nm laser excitation and using band path filters of 670±7 nm and 780±30 nm. Results were processed using FCS Express 4 (De Novo Software, USA).

Spectroflourimetry: $10^7$/ml Live or inactivated bacteria in PBS were stained with FM® 1-43 (43N-(3-Triethylammoniumpropyl)-4-(4-(Dibutylamino) Styryl) Pyridinium Dibromide) or FM® 4-64 (N-(3-Triethylammoniumpropyl)-4-(6-(4-(Diethylamino) Phenyl) Hexatrienyl) Pyridinium Dibromide) as described. Bacteria were centrifuged (14,000 rpm, 3 min) and re-suspended in 1 ml PBS. 250 µl of bacteria solution were transferred to dark 96 well plate (BrandTech Scientific). Samples stained with FM® 1-43 (43N-(3-Triethylammoniumpropyl)-4-(4-(Dibutylamino) Styryl) Pyridinium Dibromide) were excited with 490 nm and fluorescence spectrum was measured between 520 nm and 700 nm (Synergy H1 Multi-Mode Reader, Bio-Tek, Canada). Samples stained with FM® 4-64 (N-(3-Triethylammoniumpropyl)-4-(6-(4-(Diethylamino) Phenyl) Hexatrienyl) Pyridinium Dibromide) were excited with 490 nm and fluorescence spectrum was measured between 530 nm and 850 nm (Infinite 200 Pro, Tecan, Switzerland).

EXAMPLES

The following examples illustrate the invention, and are not intended to be limiting.

Figure 2:
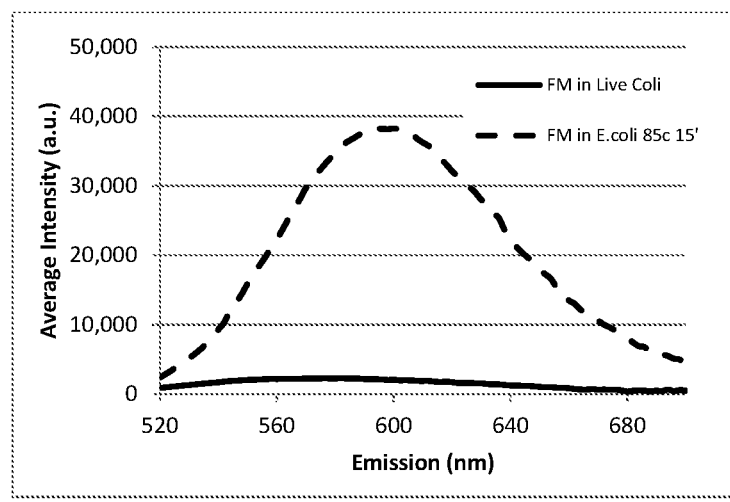
FIG. 2 shows fluorescence spectra of: the styryl dye FM® 1-43 (43N-(3-Triethylammoniumpropyl)-4-(4-(Dibutylamino) Styryl) Pyridinium Dibromide) in stained bacteria: E. coli #8739, $10^7$ cfu/ml in a logarithmic phase, washed and re-suspended in PBS (solid line) and the same bacteria after inactivation in 85° C. for 15 min (dash line). Bacterial staining was done in 4.9 µM FM® 1-43 (43N-(3-Triethylammoniumpropyl)-4-(4-(Dibutylamino) Styryl) Pyridinium Dibromide) for 5 min, and washing out the excess dye by centrifugation steps. Excitation was done at 488 nm
Figure 3:
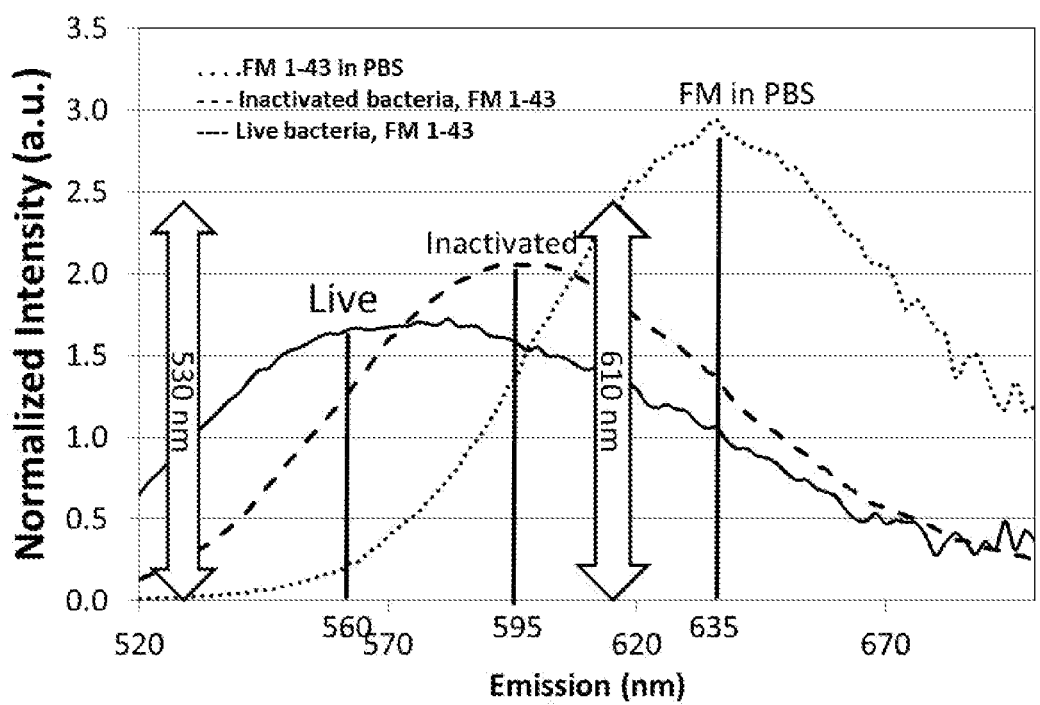
FIG. 3 shows normalized fluorescence spectra of: the styryl dye FM® 1-43 (43N-(3-Triethylammoniumpropyl)-4-(4-(Dibutylamino) Styryl) Pyridinium Dibromide) in PBS (dotted line). E. coli #8739, $10^7$ cfu/ml in a logarithmic phase, washed and re-suspended in PBS (solid line). The same bacteria after inactivation in 85° C. for 5 min (dash line). Bacterial staining was done in 4.9 microM FM® 1-43 (43N-(3-Triethylammoniumpropyl)-4-(4-(Dibutylamino) Styryl) Pyridinium Dibromide) for 5 min, washing out the excess dye by centrifugation steps. Excitation was done at 488 nm. The double arrows indicate the chosen wavelength for SIR calculation at 530 and 610 nm respectively.

Example 1—Scanning Fluorescence Results for FM® 1-43 (43N-(3-Triethylammoniumpropyl)-4-(4-(Dibutylamino) Styryl) Pyridinium Dibromide) Stained Bacteria The fluorescence spectra of the styryl dye (FM® 1-43 (43N-(3-Triethylammoniumpropyl)-4-(4-(Dibutylamino) Styryl) Pyridinium Dibromide)) and the stained bacteria in PBS are presented in the fluorescence spectra in FIG. 2 and in its normalized form in FIG. 3 for enhancing the visibility of the spectral changes. It is clearly shown that the maximum emission peak of the dye is shifted in the live bacteria towards the blue, compare to the inactivated bacteria and to the free dye. The maximal peaks are: 635 nm—free dye, 595 nm for the inactivated bacteria and 560 nm for the live bacteria. It is also shown that the intensity of the fluorescence is lower in the live bacteria, with I=3000 at 560 nm, compare to the inactivated bacteria, where I=40,000 at 595 nm. It is therefore evident that differentiation between live and inactivated bacterial populations can be made using the two parameters—the spectral shift and intensity. To quantify the phenomena the ratio between the fluorescence intensities in the two distinct wavelength, which will reflect the maximum effect and be useful for future implementation, was calculated. The selected wavelength as marked in FIG. 3 are 530 nm and 610 nm. The Intensity values of these wavelength are presented in Table 1. One can see that for the inactivated bacteria the fluorescence intensity increased 4 fold in 530 nm and 20 fold in 610 nm. This indicates that not only there is increased fluorescence staining in the dead bacteria but the fluorescence spectra is shifted. The different enhancement in the two wavelengths for the inactivated bacteria compared to the live bacteria enable us to calculate the SIR and the NVP, and summarize in Table 1.

Figure 4:
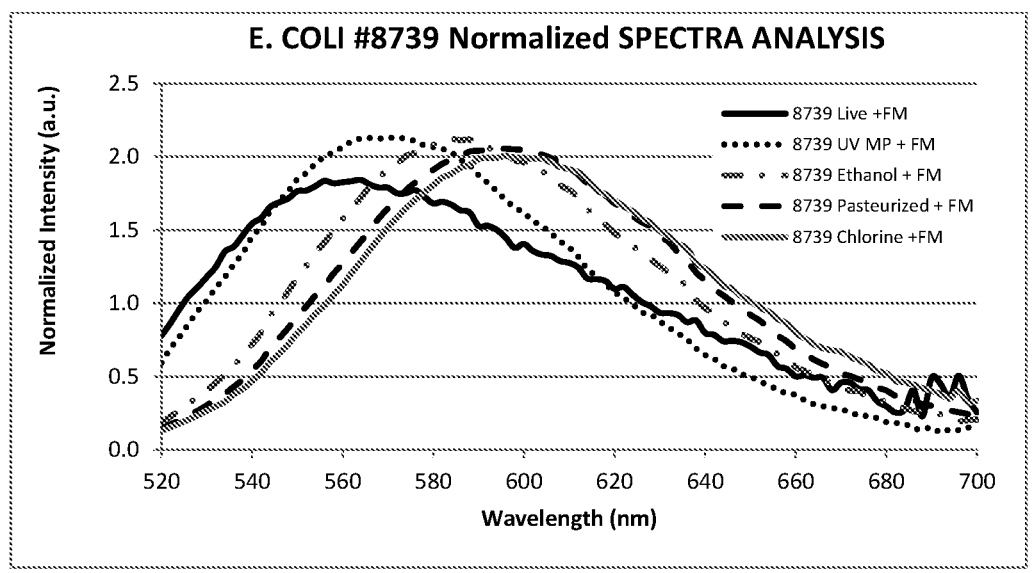
FIG. 4 shows normalized fluorescence spectra of FM® 1-43 (43N-(3-Triethylammoniumpropyl)-4-(4-(Dibutylamino) Styryl) Pyridinium Dibromide) stained E. coli #8739, $10^7$/ml after different inactivation methods, as labeled.

The same spectral analysis was obtained in different inactivation methods such as Chlorine inactivation, heating, Ethanol and UV irradiation by medium pressure and low pressure. For the method the viability reduced in 5 to 6 logs as shown by cfu method. The overlay of the outcome fluorescence spectra is shown in FIG. 4, and summarized in Table 1. One can notice that in all the method, except for the UV-LP, the NVP >1, which correlate to the non-viability state of the bacteria as demonstrated in cfu. Treating the bacteria by UV-LP indeed causes their inactivation (5 logs) however SIR effect didn't occur, this is probably due to the fact that in UV-LP the irradiation is limited to 254 nm where only DNA is damaged and not the protein or the cell membrane. It is known that UV irradiation can damage DNA, leading to cells that are unable to replicate, but remain able to metabolize for a period of time.

TABLE 1

SIR and NVP calculation from the fluorescence intensities values derived from the fluorimeter measurements of *E. coli* - FM 1-43 staining*

| Wavelength | Live | 85°, 15 min | Chlorine 0.05% | Ethanol 70% | UV-MP** 30 mJ | UV-LP 30 mJ |
|---|---|---|---|---|---|---|
| SIR ($I_{610}/I_{530}$) | ~1.5 | ~7 | ~8 | 4.4 | 3.7 | 1 |
| Non-Viability Parameter (NVP) | | ~5 | ~5 | ~3 | ~2 | 1 |

*All samples must contain same bacterial concentration for comparable intensity measurements.
**Irradiation of the bacteria with medium pressure UV (UV-MP) at the range of 200-300 nm results in reduce viability of at least 5 log in the range of 4 to 70 mJ. Irradiation with low pressure UV (UV-LP) also result in the bacterial inactivation but with no SIR effect.

Example 2—Flow Cytometry Results FM® 1-43 (43N-(3-Triethylammoniumpropyl)-4-(4-(Dibutylamino) Styryl) Pyridinium Dibromide) Stained Bacteria Although fluorimeter measurements are quantitate, it is a macroscopic measurement of the total sample, hence it is dependent on the bacteria concentration in the solution. To verify that the phenomena can be detected also with a single bacteria, Flow-Cytometry measurements of the stained bacterial samples were performed. In order to adjust the Flow-Cytometry to the spectral characterization as shown in the fluorescence spectra of the FM® 1-43 (43N-(3-Triethylammoniumpropyl)-4-(4-(Dibutylamino) Styryl) Pyridinium Dibromide) stained bacteria, the 488 nm excitation channel of the flow-cytometry and two fluorescence channel using 530 (30) nm and 610 (20) nm as the λ1 and λ2 for the SIR calculation were used.

Figure 5:
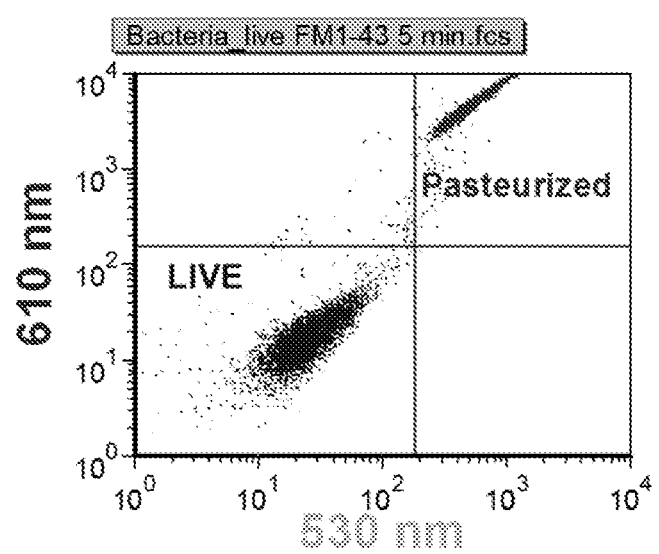
FIG. 5 is a Flow-Cytometry dot plots overlay of two bacterial (E. coli #8739, $10^7$ cfu/ml) samples after FM® 1-43 (43N-(3-Triethylammoniumpropyl)-4-(4-(Dibutylamino) Styryl) Pyridinium Dibromide) staining (left down quadrant) Live bacteria; (right up quadrant) Heated bacteria (pasteurized—85° C., 15 min)), as visualized with fluorescent activated cell sorting. The flow cytometry dot plot is gated by light scatter parameters (FSC/SSC) for the bacterial population, the fluorescence filters are 530(30) nm and 610(20) nm. Excitation is by 488 nm laser.

In FIG. 5 the overlay dot plots of live bacteria, *E. coli*, vs. inactivated (by heat) bacteria is shown on the fluorescence parameter of 610/530 nm. It is clear that the inactivated population has enhanced fluorescence in both wavelength 610 nm and 530 nm, which is more dominant in the 610 nm.

Figure 6:
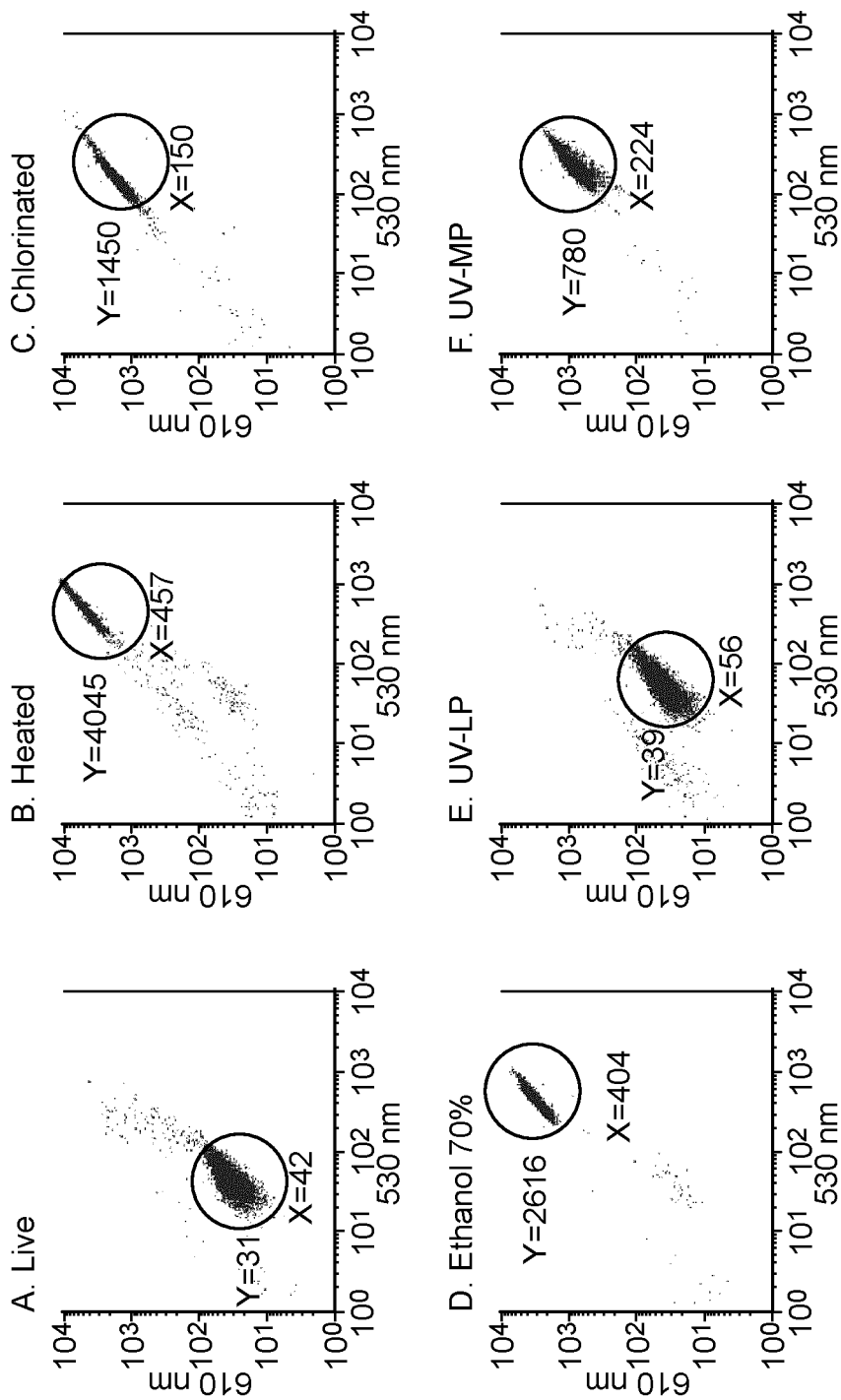
FIGS. 6A-6F shows separated dot plots of E. coli #8739 ($10^7$ cfu/ml) samples after FM® 1-43 (43N-(3-Triethylammoniumpropyl)-4-(4-(Dibutylamino) Styryl) Pyridinium Dibromide) staining.

The process described was repeated with the same bacteria for five different inactivation procedures and their fluorescence results shown in the scanning fluorimeter above and here in the flow cytometry analysis of the 610/530 nm emission filters. The resulted dot plots for the different bacterial status flow-cytometry analysis is presented in FIG. 6. For each dot plot the gated population represent the bacteria and its mean fluorescence emission for 530 and 610 nm is shown as X and Y respectively. From these values the SIR can be calculated. For example for live bacteria the mean fluorescence intensities are: $I_{530}$=42 and $I_{610}$=31 to yield $SIR_{live}$=0.73. For the heated inactivated bacteria the mean fluorescence are: $I_{530}$=457 and $I_{610}$=4045 to yield $SIR_{heated}$=8.8. Hence the NVP for the heated bacteria would be 9. The rest of the samples SIR and NVP values are summarized in Table 2. In all cases of inactivated bacteria the SIR and consequently the NVP values are greater than 1 except for the UV-LP treated bacteria. Moreover, the concluded data from the flow-cytometry are in line with the data from fluorimeter measurements. Although somewhat different, it does show a similar magnitude and trend.

The UV-LP irradiation (limited to 254 nm) causes inactivation of the bacteria only by DNA damage with no membrane or protein inactivation, likely maintaining the bacterial structure at the molecular level. Thus, UV-LP irradiation inactivation may not result in inactivated bacteria with different staining of the FM® 1-43 (43N-(3-Triethylammoniumpropyl)-4-(4-(Dibutylamino) Styryl) Pyridinium Dibromide) when compared to live bacteria. However, UV-LP is not a recommended treatment for bacteria in large water treatment. Indeed, for large water treatment UV-MP treatment is recommended by the authorities such as EPA; for UV-MP the calculated NVP was 5.

TABLE 2

SIR and NVP calculation from the fluorescence intensities values derived from the Flow-Cytometry measurements of *E. coli* - FM 1-43 staining

| Wavelength | Live | 85°, 15 min | Chlorine 0.05% | Ethanol 70% | UV-MP** 30 mJ | UV-LP 30 mJ |
|---|---|---|---|---|---|---|
| SIR (610/530) Ratio | 0.73 | 8.8 | 9.6 | 6.5 | 3.5 | 0.7 |
| Non-Viability Parameter (NVP) | | 9 | 10 | 7 | 5 | 1 |

Example 3—FM® 4-64 (N-(3-Triethylammoniumpropyl)-4-(6-(4-(Diethylamino) Phenyl) Hexatrienyl) Pyridinium Dibromide) Stained Bacteria Another member of the styryl dyes is Synaptored or FM® 4-64 (N-(3-Triethylammoniumpropyl)-4-(6-(4-(Diethylamino) Phenyl) Hexatrienyl) Pyridinium Dibromide) which is characterized in longer hydrophobic region and bathochromic emission characterization (at λmax=750 nm) then the FM® 1-43 (43N-(3-Triethylammoniumpropyl)-4-(4-(Dibutylamino) Styryl) Pyridinium Dibromide).

Figure 7:
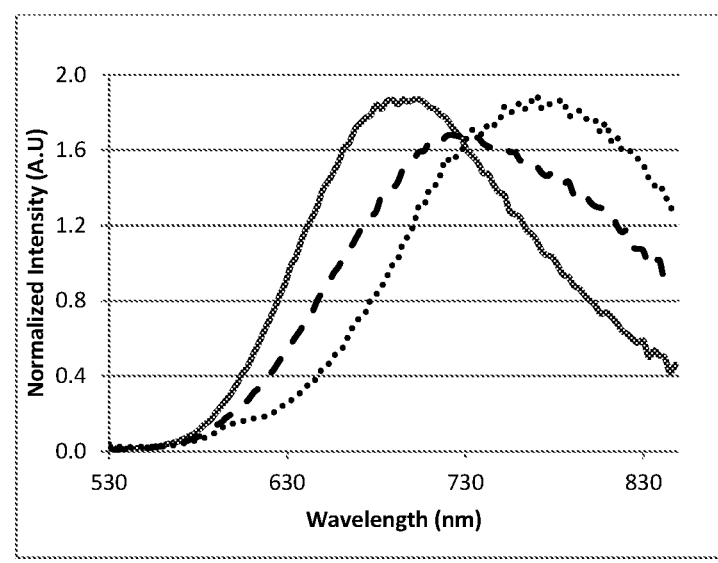
FIG. 7 shows normalized fluorescence spectra of FM® 4-64 (N-(3-Triethylammoniumpropyl)-4-(6-(4-(Diethylamino) Phenyl) Hexatrienyl) Pyridinium Dibromide) stained E. coli #8739, $10^7$/ml after different inactivation methods, black solid line—live, dash line—heated, dotted line—chlorinated.
Figure 8:
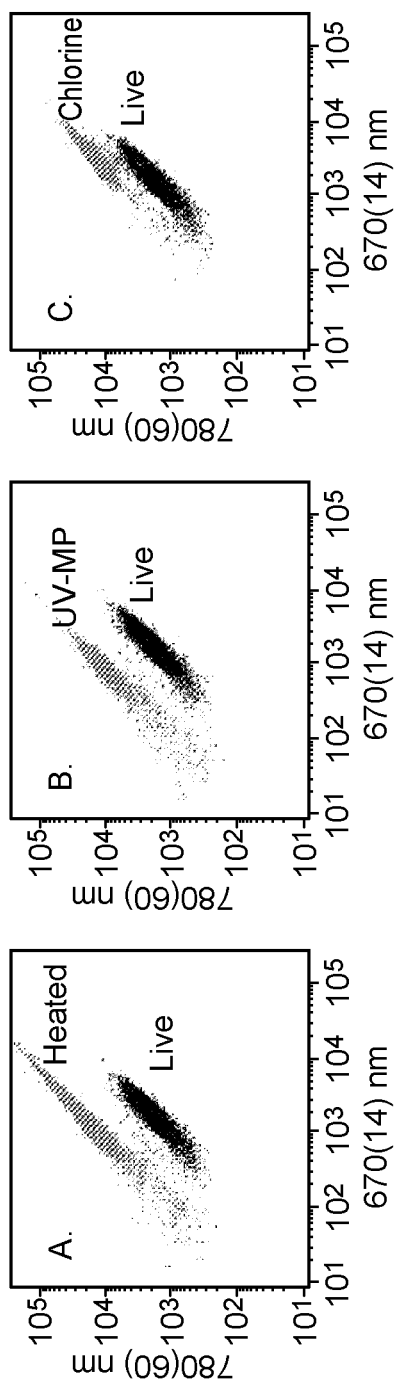
FIGS. 8A-C is a dot plot overlays of bacterial (E. coli #8739, $10^7$ cfu/ml) samples after FM® 4-64 (N-(3-Triethylammoniumpropyl)-4-(6-(4-(Diethylamino) Phenyl) Hexatrienyl) Pyridinium Dibromide) staining.

In FIG. 7 one can observe the resulting normalized fluorescence spectra of live, heated (85°, 15 min) and chlorinated stained *E. coli* with the FM® 4-64 (N-(3-Triethylammoniumpropyl)-4-(6-(4-(Diethylamino) Phenyl) Hexatrienyl) Pyridinium Dibromide). For the live bacteria the maximum emission peak is shifted to 690 nm, for the inactivated bacteria maximum emission peak are at 740 and 760 nm respectively. From the spectra one can define two wavelength for calculating SIR, which are at 780 nm and 670 nm. These wavelength were used as optical filters in a Flow Cytometry set up for the SIR analysis per single bacteria. In FIG. 8 we can see the dot-plots overlay of live, heated, and chlorinated bacterial population on the 670(14)/780(60) nm emission channels. As can be seen the inactivated bacterial population is in the low 670/780 channels where for the inactivated bacterial population the emission on the 780 (60) nm channel is increased. For calculating the SIR was derived from the flow cytometry statistic the mean fluorescence intensity in both wavelength to calculate the SIR values and the NVP. These values, Table 3, show correlation between the inactivation states of the bacteria to the NVP value, as for the inactivated bacteria NVP >1.

Comparing the NVP values of E. coli stained with FM® 4-64 (N-(3-Triethylammoniumpropyl)-4-(6-(4-(Diethylamino) Phenyl) Hexatrienyl) Pyridinium Dibromide) to FM® 1-43 (43N-(3-Triethylammoniumpropyl)-4-(4-(Dibutylamino) Styryl) Pyridinium Dibromide) reveals more distinct values for FM® 1-43 (43N-(3-Triethylammoniumpropyl)-4-(4-(Dibutylamino) Styryl) Pyridinium Dibromide), however both dyes show NVP >1, hence can be used to discriminate Live/Inactivated bacteria.

TABLE 3

SIR and NVP calculation by Flow-Cytometry analysis at 670 (14)/780 (60) nm channels for FM 4-64 stained E. coli #8739. For the heated and chlorinated bacteria cfu results show 6 log decreasing.

| Bacteria status | SIR calculation | NVP calculation |
|---|---|---|
| Live | 3.5 | |
| Heated (85°, 15 min) | 14 | 4 |
| UV-MP | 13 | 3.7 |
| Chlorinated | 12 | 3.4 |

Example 4—Gram Positive Bacteria

Gram positive bacteria are different in their membrane structure from Gram negative by having thicker peptidoglycan layer on the outer side of the cell membrane where in the Gram negative the thin peptidoglycan is inside an outer cell membrane. Since the type of staining presented here is membrane dependent, it was expected that gram positive bacteria would behave differently from gram negative bacteria. We have observed that for gram positive bacteria the phenomena is weaker with the FM® 1-43 (43N-(3-Triethylammoniumpropyl)-4-(4-(Dibutylamino) Styryl) Pyridinium Dibromide) dye and it is more dominant using the more lypophylic dye, FM® 4-64 (N-(3-Triethylammoniumpropyl)-4-(6-(4-(Diethylamino) Phenyl) Hexatrienyl) Pyridinium Dibromide).

While differences were observed, we were surprised that both gram positive and negative bacteria can examined in this method.

Figure 9:
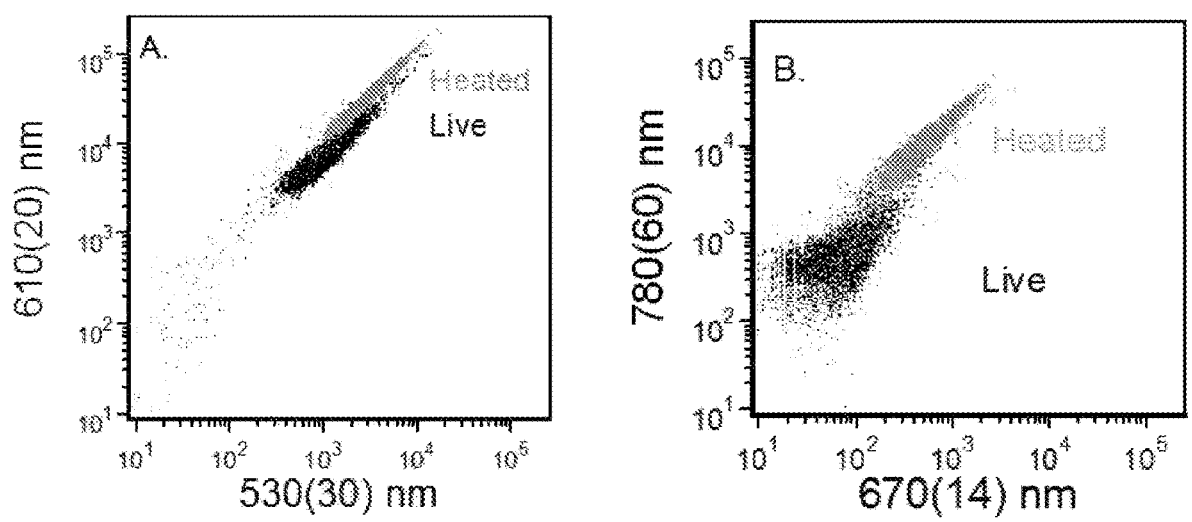
FIGS. 9A-B is a dot plot overlays of E. faecalis, $10^7$ cfu/ml live, black dots, and heated (85° C., 15 min), gray dots, stained with (FIG. 9A) FM® 1-43 (43N-(3-Triethylammoniumpropyl)-4-(4-(Dibutylamino) Styryl) Pyridinium Dibromide) and (FIG. 9B) with FM® 4-64 (N-(3-Triethylammoniumpropyl)-4-(6-(4-(Diethylamino) Phenyl) Hexatrienyl) Pyridinium Dibromide).

As an example to Gram positive bacteria Enterococcus faecalis bacteria, which is an important water infectious indicator has been stained and analyzed by fluorimeter analysis (data not shown) and flow cytometry analysis. In FIG. 9 the flow cytometry analysis of the stained E. faecalis as live and inactivated by heat are presented, both by FM® 1-43 (43N-(3-Triethylammoniumpropyl)-4-(4-(Dibutylamino) Styryl) Pyridinium Dibromide) (A) and FM® 4-64 (N-(3-Triethylammoniumpropyl)-4-(6-(4-(Diethylamino) Phenyl) Hexatrienyl) Pyridinium Dibromide) (B) staining. Other means of inactivation like chlorine and UV_MP show similar dot plots overlay. It is clear that in both staining there are different SIR for the inactivated compare to the live bacteria, with a stronger effect using the FM® 4-64 (N-(3-Triethylammoniumpropyl)-4-(6-(4-(Diethylamino) Phenyl) Hexatrienyl) Pyridinium Dibromide) staining. The SIR and NVP were calculating by using the flow-cytometry gating statistic data and presented in FIG. 9. Both FM® 1-43 (43N-(3-Triethylammoniumpropyl)-4-(4-(Dibutylamino) Styryl) Pyridinium Dibromide) and FM® 4-64 (N-(3-Triethylammoniumpropyl)-4-(6-(4-(Diethylamino) Phenyl) Hexatrienyl) Pyridinium Dibromide) show NVP >1 for the inactivated bacteria with a higher results for the FM® 4-64 (N-(3-Triethylammoniumpropyl)-4-(6-(4-(Diethylamino) Phenyl) Hexatrienyl) Pyridinium Dibromide). Better Live/Inactivated discrimination with the more hydrophobic dye is, thus, demonstrated.

TABLE 4

SIR and NVP calculation by Flow-Cytometry analysis for E. faecalis Live and inactivated (heated and chlorine) after FM ® 1-43 (43N-(3-Triethylammoniumpropyl)-4-(4-(Dibutylamino) Styryl) Pyridinium Dibromide) and FM ® 4-64 (N-(3-Triethylammoniumpropyl)-4-(6-(4-(Diethylamino) Phenyl) Hexatrienyl) Pyridinium Dibromide) staining. Inactivated bacteria are 5-6 log decreased by cfu.

| | | Live | Heated | Chlorine | UV-MP |
|---|---|---|---|---|---|
| FM ® 1-43(43N-(3-Triethylammoniumpropyl)-4-(4-(Dibutylamino) Styryl) Pyridinium Dibromide) | SIR: 530(30)/610(20) | 6.5 | 10.3 | 13 | 7.1 |
| | NVP | | 1.6 | 2 | 1.1 |
| FM ® 4-64 (N-(3-Triethylammoniumpropyl)-4-(6-(4-(Diethylamino) Phenyl) Hexatrienyl) Pyridinium Dibromide) | SIR: 670(14)/780(60) | 6.7 | 20 | 19.7 | 8.1 |
| | NVP | | 3 | 2.9 | 1.2 |

Example 5—Expanding the Effect Across Several Bacteria

All Gram negative have significant SIR effect for all inactivation methods in here: UV-MP, Heating and Chlorinated.

FM® 1-43 (43N-(3-Triethylammoniumpropyl)-4-(4-(Dibutylamino) Styryl) Pyridinium Dibromide) is preferred than FM® 4-64 (N-(3-Triethylammoniumpropyl)-4-(6-(4-(Diethylamino) Phenyl) Hexatrienyl) Pyridinium Dibromide) for Gram negative.

Gram positive show SIR effect weaker but positive, better in FM® 4-64 (N-(3-Triethylammoniumpropyl)-4-(6-(4-(Diethylamino) Phenyl) Hexatrienyl) Pyridinium Dibromide).

For UV-MP results are low.

UV-LP—no effect

TABLE 5

NVP values, calculated by Flow-Cytometry analysis of several Gram negative and positive bacteria by FM ® 1-43 (43N-(3-Triethylammoniumpropyl)-4-(4-(Dibutylamino) Styryl) Pyridinium Dibromide) and FM ® 4-64 (N-(3-Triethylammoniumpropyl)-4-(6-(4-(Diethylamino) Phenyl) Hexatrienyl) Pyridinium Dibromide) staining

| | | Staining | | | | | |
|---|---|---|---|---|---|---|---|
| | | FM ® 1-43 (43N-(3-Triethylammoniumpropyl)-4-(4-(Dibutylamino) Styryl) Pyridinium Dibromide) | | | FM ® 4-64 (N-(3-Triethylammoniumpropyl)-4-(6-(4-(Diethylamino) Phenyl) Hexatrienyl) Pyridinium Dibromide) | | |
| Inactivation Bacteria | | Chlorine | Heated | UV-MP | Chlorine | Heated | UV-MP |
| Coliform | *E. coli* - #8739 | 10 | 9 | 5 | 3.4 | 4 | 3.7 |
| | *E. coli* - #25922 | 9 | 7 | 5 | | | |
| | *E. coli* - O157 | ~10 | ~10 | Nd | | | |
| | *Entrobacter cloacae* | 10 | 8 | 5 | 4.5 | 3.7 | 2.5 |
| | *Entrobacter aerogenes* | 12 | 8 | 4.5 | 4.5 | 3.3 | 1.7 |
| | *Pseudomonas aeruginosa* | 5 | 4.6 | 3.2 | 2 | 1.8 | |
| Gram Positive | *Enterococcus faecalis* | 2 | 1.6 | 1.1 | 2.9 | 3 | 1.2 |
| | *Bacillus subtillis* | 1.5 | 1.2 | 1.2 | 1.5 | 1.8 | |
| | *Enterococcus faecium* | 1.7 | 1.6 | Nd | 3 | 3 | |
| | *S. aureus* | 1.7 | 1.6 | 1.1 | 2.4 | 3 | 1.1 |

Counting bacteria: The double fluorescence analysis and the SIR effect of the bacteria by the FM® 1-43 (43N-(3-Triethylammoniumpropyl)-4-(4-(Dibutylamino) Styryl) Pyridinium Dibromide) or FM® 4-64 (N-(3-Triethylammoniumpropyl)-4-(6-(4-(Diethylamino) Phenyl) Hexatrienyl) Pyridinium Dibromide) staining and flow cytometry analysis enable to discriminate the events representing live bacteria from other events representing debris, aggregate and inactivated bacteria as described. These events, corresponding to the NVP of live bacteria, are counted during the flow-cytometry analysis. The concentration of the samples can be derived by knowing the flow rate and the time of analysis of each samples, as previously described in the literature. Equation 1 translates the event count (g) to bacteria concentration per ml (C):

$$[C] = g*1000/(\text{flow rate})*\text{time}. \quad \text{Equation 1:}$$

Where flow rate is in microL/min, and time is in min.

Figure 10:
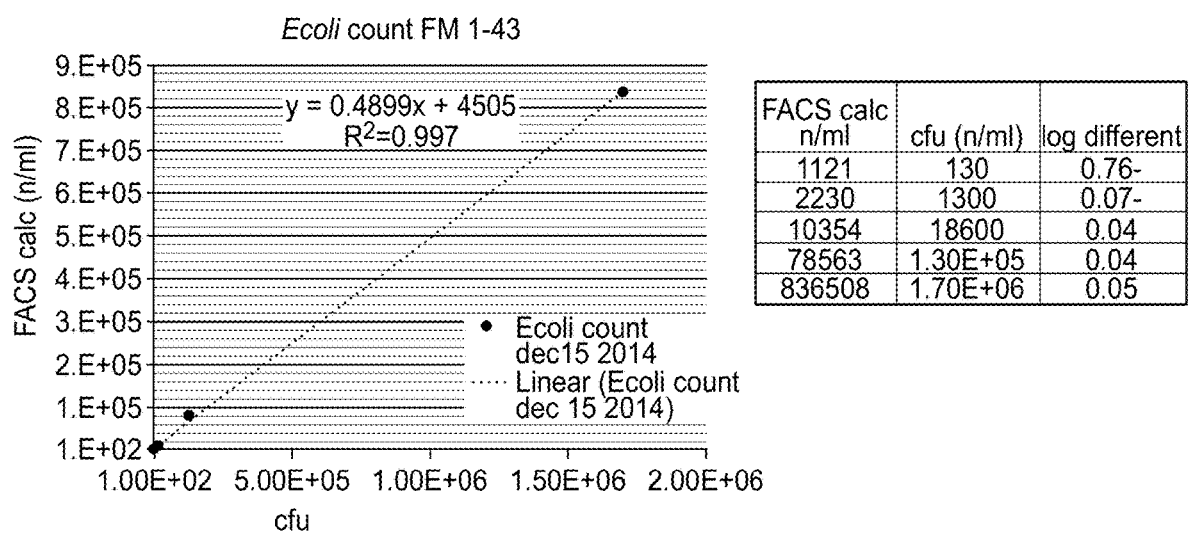
FIG. 10 is a graph correlation of bacterial concentration between the flow-cytometry and FM® 1-43 (43N-(3-Triethylammoniumpropyl)-4-(4-(Dibutylamino) Styryl) Pyridinium Dibromide) calculation and cfu. Including the calculated number and the log error between the measurements in the small table.
Figure 11:
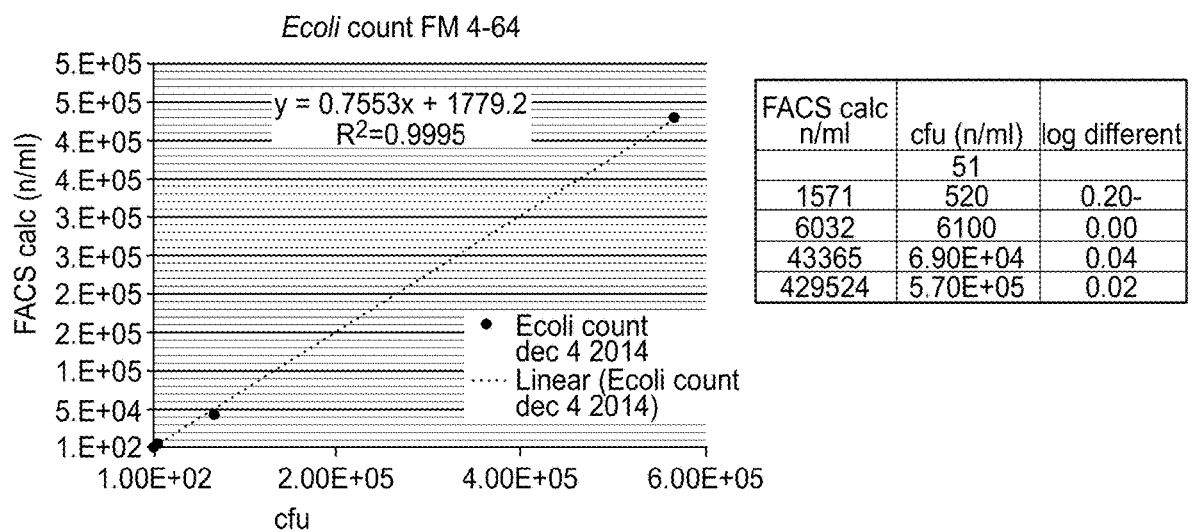
FIG. 11 depicts a graph correlation of bacterial concentration between the flow-cytometry and FM® 4-64 (N-(3-Triethylammoniumpropyl)-4-(6-(4-(Diethylamino) Phenyl) Hexatrienyl) Pyridinium Dibromide) calculation and cfu. Including the calculated number and the log error between the measurements in the small table.

The results are presented for FM® 1-43 (43N-(3-Triethylammoniumpropyl)-4-(4-(Dibutylamino) Styryl) Pyridinium Dibromide) and FM® 4-64 (N-(3-Triethylammoniumpropyl)-4-(6-(4-(Diethylamino) Phenyl) Hexatrienyl) Pyridinium Dibromide) staining in FIG. 10 and respectively FIG. 11. There is very high correlation ($r^2 > 0.99$) between the two methods on the range of 1000 to $10^6$ bacteria. In the low level of less than 1000 the noise may outnumber the signal without any ability to discriminate noise from bacteria. In all concentrations (between 1000 to million) the error is less than 0.5 Log as accepted in microbiological counting.

Example 7—Microscopy Results

Figure 12:
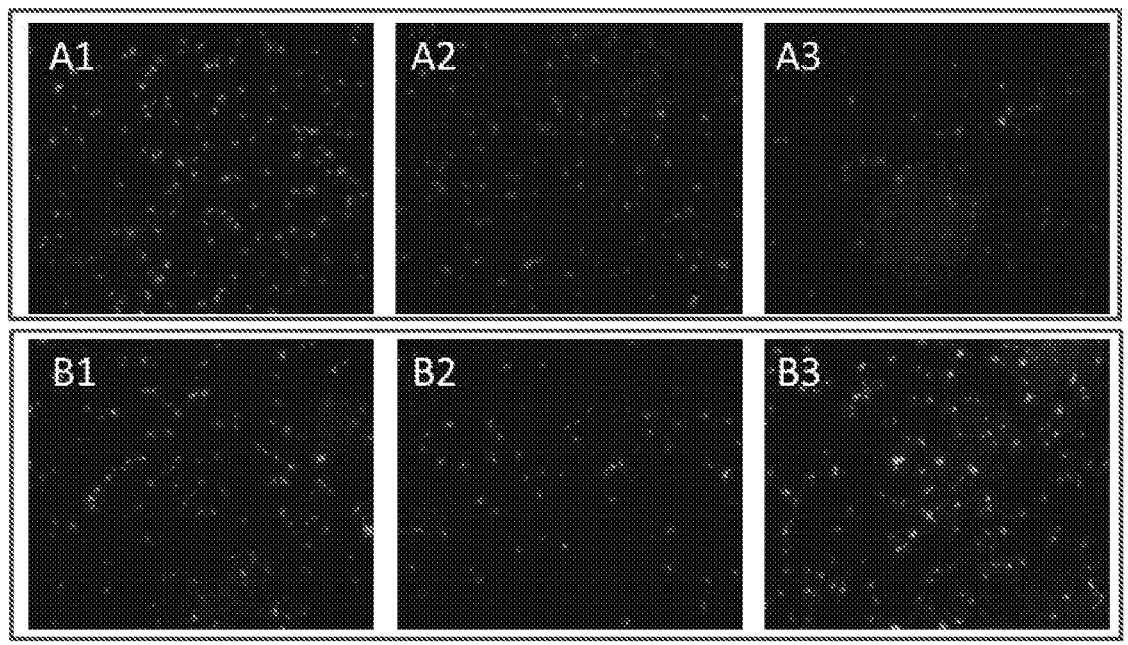
Figure 13:
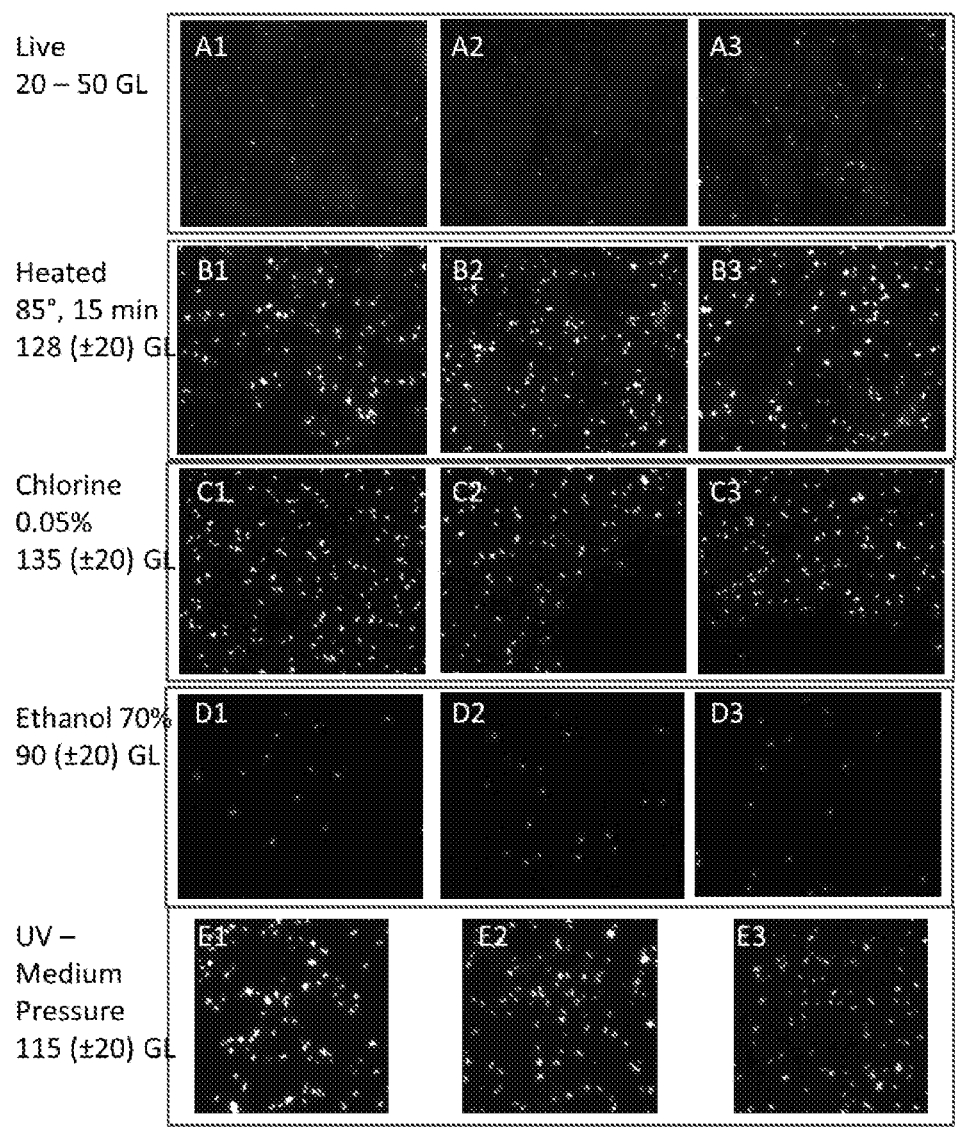
FIGS. 13A-13E was produced using microscopy fluorescence imaging, Excitation.=470 nm, Emission=600(50) nm, of E. coli FM® 1-43 (43N-(3-Triethylammoniumpropyl)-4-(4-(Dibutylamino) Styryl) Pyridinium Dibromide) stained.

Observing live bacteria and inactivated bacteria in the standard emission filter, 525(50) nm, in the fluorescence microscope shows that there is little difference in intensity, see FIG. 12, which is in line with the findings of the present invention. When observing the fluorescence bacteria thru the 600(50) nm emission filter, the change in intensity from 20-50 GL in live bacteria to the range of 90-150 in different inactivated bacteria, FIG. 13, is evident.

Example 8—*E. coli* K12 with Ampicillin

The disclosed method was further validated in studies using *E. coli* K12 (MG1655, obtained from ATCC). After 5 hours of growth in medium, *E. coli* were divided into three groups: (A) grown for one hour with no antibiotics, (B) grown for one hour with 700 micrograms of ampicillin, and (C) grown for one hour with 1500 micrograms of ampicillin. The bacteria were suspended in PBS and stained with FM® 1-43 (43N-(3-Triethylammoniumpropyl)-4-(4-(Dibutylamino) Styryl) Pyridinium Dibromide) (5 as per the methodology described earlier.

Figure 14:
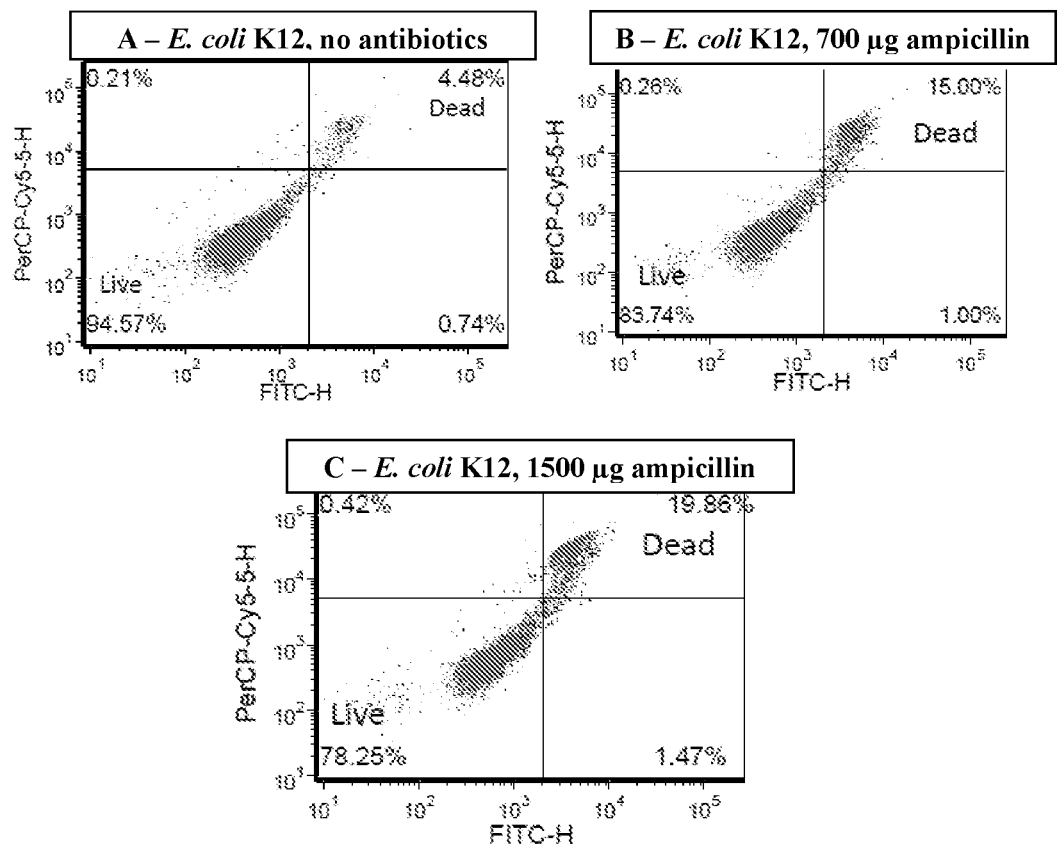
FIGS. 14A-14C is a flow-cytometry dot plot of E. coli K12 grown for 5 hours followed by (FIG. 14A) 1 hour without antibiotic, (FIG. 14B) 1 hour with 700 µg ampicillin, and (FIG. 14C) 1 hour with 1500 µg ampicillin.

Flow-Cytometry measurements of the stained bacterial samples were performed. In order to adjust the flow-cytometry to the spectral characterization as shown in the fluorescence spectra of the FM® 1-43 (43N-(3-Triethylammoniumpropyl)-4-(4-(Dibutylamino) Styryl) Pyridinium Dibromide) stained bacteria, the [CONFIRM: 488] nm excitation channel of the flow-cytometry and two fluorescence channel using 530 (30) nm and 610 (20) nm as the λ1 and λ2 for the SIR calculation were used. The results are tabulated below and depicted in FIG. 14.

TABLE 6

SIR calculation by Flow-Cytometry analysis for *E. coli* K12

| | No antibiotic (A) | | 700 µg ampicillin (B) | | 1500 µg ampicillin (C) | |
|---|---|---|---|---|---|---|
| | LIVE | DEAD | LIVE | DEAD | LIVE | DEAD |
| % from population | 94.6% | 4.5% | 83.7% | 15% | 78% | 20% |
| 530 nm | 395 | 4575 | 463 | 4215 | 566 | 4011 |
| 610 nm | 387 | 16264 | 440 | 18753 | 559 | 21370 |
| SIR | 1 | 3.55 | 1 | 4.4 | 1 | 5.3 |

These data demonstrate that the SIR technique is applicable to bacteria killed or inactivated by antimicrobial drugs.

What is claimed is:

1. A method of differentiating between live and inactivated bacteria in a treated sample comprising:

staining the sample with a N-(3-Triethylammoniumpropyl)-4-(4-(Dibutylamino) Styryl) Pyridinium Dibromide dye;

illuminating the sample with an incident light at an excitation wavelength of 488 nm, wherein an illuminated live bacteria stained with the N-(3-Triethylammoniumpropyl)-4-(4-(Dibutylamino) Styryl) Pyridinium Dibromide dye exhibits a first maximum emission peak, and wherein an illuminated inactivated bacteria stained with the N-(3-Triethylammoniumpropyl)-4-(4-(Dibutylamino) Styryl) Pyridinium Dibromide dye exhibits a second maximum emission peak that is shifted compared to the first maximum emission peak;

measuring, for each bacterial cell (i) the intensity I1 of emitted light at wavelength 1 of 530 nm and (ii) the intensity I2 of emitted light at wavelength 2 of 610 nm;

calculating a ratio I2/I1; and determining that a bacterial cell is live when I2/I1<2.0 and determining that the bacterial cell is inactivated when I2/I1>2.0.

2. A method of differentiating between live and inactivated bacteria in a treated sample comprising:

staining the sample with a N-(3-Triethylammoniumpropyl)-4-(6-(4-(Diethylamino) Phenyl) Hexatrienyl) Pyridinium Dibromide dye;

illuminating the sample with an incident light at excitation between 488 and 570 nm, wherein an illuminated live bacteria stained with the N-(3-Triethylammoniumpropyl)-4-(6-(4-(Diethylamino) Phenyl) Hexatrienyl) Pyridinium Dibromide dye exhibits a first maximum emission peak, and wherein an illuminated inactivated bacteria stained with the N-(3-Triethylammoniumpropyl)-4-(6-(4-(Diethylamino) Phenyl) Hexatrienyl) Pyridinium Dibromide dye exhibits a second maximum emission peak that is shifted compared to the first maximum emission peak;

measuring, for each bacterial cell (i) the intensity I1 of emitted light at wavelength 1 of 670 nm and (ii) the intensity I2 of emitted light at wavelength 2 of 780 nm;

calculating a ratio I2/I1; and determining that a bacterial cell is live when I2/I1<2.0 and determining that the bacterial cell is inactivated when I2/I1>2.0.

3. The method of claim 1, further comprising treating live bacteria cells contained in the sample in an effort to inactivate the bacteria cells prior to the staining step.

4. The method of claim 3, further comprising the step of filtering the stained cells prior to the illuminating step and subsequent to the staining step.

5. The method of claim 3, wherein the treating step comprises interacting the live bacteria with an antimicrobial drug.

6. The method of claim 3, wherein the treating step comprises heating, adding an antibiotic drug, adding an antibacterial drug, adding ethanol or ultraviolet (UV) irradiation.

7. The method of claim 2, further comprising treating live bacteria cells contained in the sample in an effort to inactivate the bacteria cells prior to the staining step.

8. The method of claim 7, further comprising the step of filtering the stained cells prior to the illuminating step and subsequent to the staining step.

9. The method of claim 7, wherein the treating step comprises interacting the live bacteria with an antimicrobial drug.

10. The method of claim 7, wherein the treating step comprises heating, adding an antibiotic drug, adding an antibacterial drug, adding ethanol or ultraviolet (UV) irradiation.

* * * * *

UNITED STATES PATENT AND TRADEMARK OFFICE
CERTIFICATE OF CORRECTION

PATENT NO. : 11,306,344 B2
APPLICATION NO. : 15/542922
DATED : April 19, 2022
INVENTOR(S) : Eran Zahavy It is certified that error appears in the above-identified patent and that said Letters Patent is hereby corrected as shown below:

In the Claims

Claim 2, Column 16, Line 12:
Delete:
"the intensity 11 of"
Replace with:
"the intensity I1 of"

Signed and Sealed this
Twenty-eighth Day of June, 2022

Katherine Kelly Vidal
*Director of the United States Patent and Trademark Office*